United States Patent
Hohmann et al.

[11] Patent Number: 5,166,427
[45] Date of Patent: Nov. 24, 1992

[54] PREPARATION OF ACYL CHLORIDES

[75] Inventors: Andreas Hohmann, Ludwigshafen; Enrique Freudenberg, Schifferstadt; Wolfgang Reuther, Heidelberg; Kurt Mayer, Ludwigshafen, all of Fed. Rep. of Germany

[73] Assignee: BASF Aktiengesellschaft, Ludwigshafen, Fed. Rep. of Germany

[21] Appl. No.: 719,722

[22] Filed: Jun. 24, 1991

Related U.S. Application Data

[63] Continuation of Ser. No. 418,128, Oct. 10, 1989, abandoned.

[30] Foreign Application Priority Data

Oct. 31, 1988 [DE] Fed. Rep. of Germany ....... 3836967

[51] Int. Cl.$^5$ .......................................... C07C 51/363
[52] U.S. Cl. .................... 562/857; 562/861; 562/866
[58] Field of Search .................. 562/857, 861, 866

[56] References Cited

U.S. PATENT DOCUMENTS

| | | | |
|---|---|---|---|
| 3,149,155 | 9/1964 | Seefelder | 562/857 |
| 3,547,960 | 12/1970 | Hauser | 260/408 |
| 3,857,841 | 12/1974 | Keil | 260/250 |
| 4,900,479 | 2/1990 | Freudenberg et al. | 260/408 |

FOREIGN PATENT DOCUMENTS

| | | |
|---|---|---|
| 2950155 | 7/1981 | Fed. Rep. of Germany . |
| 0103131 | 8/1981 | Japan ................... 562/857 |

OTHER PUBLICATIONS

Chem. Abstracts vol. 105, 133526, p. 637, Stammann et al., (1986).

Chem. Abstracts vol. 97, 197862, p. 544, Blank et al., (1982).
Chem. Abstracts, vol. 95, 97116, Decker et al., (1980).

Primary Examiner—Marianne M. Cintins
Assistant Examiner—Margaret J. Argo
Attorney, Agent, or Firm—John H. Shurtleff

[57] ABSTRACT

Acyl chlorides of the general formula $$R-\overset{O}{\underset{\|}{C}}-Cl \quad (I)$$

where R is $C_8$-$C_{30}$-alkyl, $C_8$-$C_{30}$-alkenyl or $C_8$-$C_{30}$-alkynyl, are prepared from a carboxylic acid of the general formula II $$R-\overset{O}{\underset{\|}{C}}-OH \quad (II)$$

where R has the abovementioned meanings, and phosgene, $COCl_2$ (III), in the presence of a catalyst adduct of phosgene and N,N-dialkylformamide of the general formula IV $$\begin{array}{c} R^1 \\ \diagdown \\ N-CHO \\ \diagup \\ R^2 \end{array} \quad (IV)$$

where $R^1$ and $R^2$ independently of one another are each $C_1$-$C_3$-alkyl, preferably a 1:1 adduct in excess N,N-dialkylformamide, the reaction product I being obtained by phase separation, by a process in which II and III are used in essentially equimolar amounts and the phase containing the catalyst adduct is reused.

10 Claims, No Drawings

PREPARATION OF ACYL CHLORIDES

This application is a continuation of application Ser. No. 418,128 filed Oct. 10, 1989, now abandoned.

Acyl chlorides can readily be prepared by reacting the corresponding carboxylic acids with phosgene. The reaction has to be catalyzed. Examples of catalysts used are carboxamides, preferably N-alkylformamides (DE-A-34 39 937).

In the case of the N,N-dialkylformamides, the size of the alkyl group ranges from dimethylformamide to formamides of 30 carbon atoms (EP-A 0 050 779, DE-A-29 50 115 and DE-A-19 31 074).

The course of the phosgenation of a carboxylic acid to the acyl chloride and the working up of the mixture is decisively influenced by the choice of the catalyst system.

As an alternative to filtration of tar-containing crude products, working up of the catalyst-containing product by distillation would also be possible in some cases. However, distillation of the resulting acyl chlorides is not only an energy-consuming and time-consuming process but also has a number of other disadvantages.

Many relatively long chain acyl chlorides cannot be distilled without partial decompostion. It is also known that the distilled products may be contaminated through decomposition of the catalyst present in the bottom product of the distillation. Larger amounts of catalyst residue constitute a safety risk during distillation, because there is a danger of spontaneous decompositon at elevated temperatures In working up impurity-containing mixtures to obtain the product, the activity of the catalyst is greatly reduced both by filtration and by distillation. In most cases, the catalyst used becomes useless, i.e. it cannot be reused.

Both distillation and filtration of catalyst-containing acyl chlorides thus constitute disadvantageous methods of working up. Because of the catalyst loss due to working up, the amount of catalyst used must be as small as possible.

In DE-A-29 50 155, the catalyst used is diisobutylformamide, which is soluble in the reaction mixture in every phase of the reaction. If a final distillation of the acyl chloride is to be dispensed with, the amount of soluble catalyst must be kept to a minimum to ensure product purity. In the case of this catalyst system too, the catalyst cannot be reused since it is discharged with the product.

It is also known that the reactions with phosgene take place more effectively the larger the amount of catalyst. Conversely, small amounts of catalyst result in either poor utilization of the gaseous phosgene used or long gassing times.

DE-A-22 40 883 describes the preparation of acyl chlorides using equimolar amounts of carboxylic acid and catalyst. However, to separate off and recover the large amount of catalyst, it is necessary finally to add benzene in an amount corresponding to 3-4 times the reaction volume and then to distill the solution of the product in benzene.

The use of large amounts of catalyst is also described in JP-10 613/68 for the preparation of linoleyl chloride using from 10 to 50 mol % of dimethylformamide, as well as from. 1 to 10 equivalents of dimethylformamide, based on linoleic acid used. The resulting acyl chloride has to be distilled and in some cases were additionally purified by treatment with active carbon. It is not intended to reuse the large amounts of catalyst In the synthesis of acyl chlorides from carboxylic acids and phosgene, it is known that the problem of removing excess phosgene from the crude acyl chloride is encountered.

According to the prior art, phosgene-containing acyl chloride can be freed from phosgene by stripping for several hours with nitrogen and/or under slightly reduced pressure. This procedure is time-consuming and has a very adverse effect on the space-time yield of the process.

In DE-A-29 50 155, the excess phosgene is distilled over with the first part of the acyl chloride distilled. In addition to a deterioration of the space-time yield, which is observed in this case too, this procedure requires additional outlay for apparatus and analysis DE-A-22 40 883 discloses a working up process in which the dilute reaction solution is washed briefly with ice water before the distillation. In view of the sensitivity of acyl chlorides to hydrolysis, this process presents problems on the industrial scale.

In the process disclosed in JP 10613/68, too, excess phosgene must be removed by working up the crude acyl chloride by distillation.

It is an object of the present invention to provide a process for the preparation of acyl chlorides which overcomes the abovementioned disadvantages.

We have found that this object is achieved by a process for the preparation of acyl chlorides of the general formula I

where R is $C_8$–$C_{30}$-alkyl, $C_8$–$C_{30}$-alkenyl or $C_8$–$C_{30}$-alkynyl, from a carboxylic acid of the general formula II

where R has the abovementioned meanings, and phosgene, $COCl_2$ (III), in the presence of a catalyst adduct of phosgene and N,N-dialkylformamide of the general formula IV

where $R^1$ and $R^2$ independently of one another are each $C_1$–$C_3$-alkyl, the reaction product I being obtained by phase separation, wherein II and III are used in essentially equimolar amounts and the phase containing the catalyst adduct is reused.

The acyl chlorides are obtainable by the following method:

Liquid or gaseous phosgene is added to the initially taken reaction mixture, consisting of carboxylic acid II and the adduct of phosgene and N,N-dialkylformamide of the formula IV. The time required for passing in gaseous phosgene can be restricted to 3-4 hours, the phosgene being virtually quantitatively utilized. There-after, the mixture is allowed to stand for from 1 to 2 hours and the phases are separated.

In this reaction, from 5 to 200, preferably from 10 to 100, particularly preferably from 10 to 30, mol % of the adduct of phosgene and N,N-dialkylformamide IV, preferably a 1:1 adduct, if necessary in excess N,N-dialkylformamide, is used, the percentages being based on the carboxylic acid II used.

The amount of phosgene III is essentially equimolar with respect to the carboxylic acid II.

The phosgene may be mixed with an inert gas. The reaction can be carried out under atmospheric, reduced or superatmospheric pressure. The reaction temperature may be from 0° to 200° C. but is preferably from 30° to 100° C., particularly preferably from 60° to 80° C.

If necessary, solvents may be added to the reaction mixture. These must be inert under the reaction conditions, examples being saturated aliphatic hydrocarbons, ethers, acetonitrile, toluene, benzene or cyclohexane.

At a temperature of from 0° to 150° C., preferably from 20° to 50° C., the lower phase formed by the catalyst is separated from the upper product phase. This can be done by a plurality of methods. For example, the catalyst can be discharged into a storage vessel until required for further use However, it is also possible to syphon the acyl chloride, i.e. the upper phase off the catalyst via a riser tube and to leave the catalyst in the reactor until the next reaction.

The acyl chloride is obtained in a quantitative amount and in high purity. It can be used without further purification, for example distillation or filtration. A particular advantage of the novel process is that the acyl chloride is free of phosgene at the end of the reaction. Hence, there is no need for any measures for removal of phosgene from the crude acyl chloride Another particular advantage of the novel process is that the catalyst can be recovered without any problems and reused.

The novel process for the preparation of acyl chlorides from aliphatic carboxylic acids is particularly suitable for monocarboxylic acids, i.e. for the preparation of compounds of the general formula RCOX, where R is an aliphatic hydrocarbon group and X is chlorine. The aliphatic group may be straight-chain or branched, saturated or olefinically or acetylenically unsaturated. Aliphatic carboxylic acids of 8 to 30, in particular 12 to 22, carbon atoms are particularly preferred.

Suitable N,N-dialkylformamides are dimethyl-, ethylmethyl-, methyl-n-propyl-, methylisopropyl-, diethyl-, ethyl-n-propyl-, ethylisopropyl-, di-n-propyl-, n-propylisopropyl- and diisopropylformamide, dimethyl- and diethylformamide being preferred and diethylformamide being particularly preferred.

EXAMPLES

EXAMPLE 1

In a thermostated 5 l reactor, 2,746 g (10 moles) of technical grade stearic acid are initially taken at 70° C. and 202 g (2 moles) of diethylformamide (DEF) are added. 1,188 g (12 moles) of gaseous phosgene are then passed in uniformly over 2.5 hours with thorough stirring. The internal temperature during the addition of phosgene is from 70° to 75° C. The waste gas from the reaction is passed directly via a scrubber, in which unconsumed phosgene is hydrolyzed.

After the end of the addition of phosgene, stirring is continued for 0.5 hour, the stirrer is switched off and the reaction mixture is transferred to a separating funnel. The vapor space above the mixture is phosgene-free (test cartridges from Dräger).

After 2 hours at 25° C., the lower catalyst phase (342 g of activated DEF) is separated off from the two-phase reaction mixture. The upper phase contains 3,900 g of stearic acid (9.89 moles 98.9% yield, based on technical grade stearic acid used) having a purity of 95% (determined by IR spectroscopy). The iodine color number (ICN) of the acyl chloride is 10. Both the acyl chloride and the catalyst are phosgene-free.

EXAMPLES 2 TO 10

To determine the efficiency of the novel process, Example 1 is repeated several times. The catalyst used in each case is the catalyst phase of the preceding experiment.

EXAMPLE 2

The experimental method described in Example 1 is used, and 2,746 g (10 moles) of technical grade stearic acid and the catalyst phase (342 g) obtained in Example 1 are initially taken. 1,089 g (11 moles) of gaseous phosgene are then introduced. The product phase contains 2,930 g (99.9% yield) of stearyl chloride having a purity of 97% (determined by IR spectroscopy); the iodine color number is 30.

Examples 3 to 10 are carried out similarly to Example 2.

| Example | Acid (moles) | Phosgene (moles) | Yield | Purity (IR) | ICN |
|---|---|---|---|---|---|
| 3 | 10.0 | 10.0 | 99% | 97% | 20 |
| 4 | 10.0 | 10.0 | 100% | 95% | 10 |
| 5 | 10.0 | 10.0 | 100% | 96% | 10 |
| 6 | 10.0 | 10.5 | 100% | 96% | 10 |
| 7 | 10.0 | 10.0 | 100% | 94% | 25 |
| 8 | 10.0 | 10.0 | 100% | 96% | 15 |
| 9 | 10.0 | 10.0 | 100% | 96% | 15 |
| 10 | 10.0 | 10.5 | 100% | 97% | 15 |

All acyl chlorides and catalysts are obtained in phosgene-free form.

EXAMPLE 11

542 g (2.0 moles) of technical grade stearic acid and 44 g of diisobutylformamide (0.28 mole) are initially taken in a reactor at 65° C., and 208 g (2.1 moles) of gaseous phosgene are passed into the melt in the course of 2.5 hours with thorough stirring The internal temperature is kept at 65° C. Stirring is then continued for 0.5 hour at 60° C.

The stearic acid is completely converted. The reaction mixture is phosgene-free. Even after the mixture has cooled to 20° C., the catalyst remains in solution in the crude acyl chloride. The amount of catalyst-containing stearic acid discharged is 624 g (maximum possible yield of stearyl chloride: 579 g). The purity of the acyl chloride is 84% (IR). The product is brown (ICN: 110).

EXAMPLE 12

In a thermostated 5 l reactor, 2,028 g (6 moles) of technical grade behenic acid are initially taken at 73° C. and 223 g (about 1.2 moles) of activated diethylformamide are added. 596 g (6.0 moles) of gaseous phosgene are then passed in uniformly over 2.75 hours with thorough stirring. The internal temperature during the addition of phosgene is from 76° to 80° C. The waste gas from the reaction is removed directly via a scrubber After the end of the reaction, the vapor space above the reaction mixture is phosgene-free.

Stirring is then continued for 1.0 hour at 77° C., the stirrer is switched off and the reaction mixture is cooled to 42° C. At this temperature, the lower catalyst phase (208 g of activated DEF) is separated off from the two-phase reaction mixture after 1.5 hours. The upper phase contains 2,122 g of behenyl chloride (99.2% yield, based on technical grade behenic acid used) having a purity of 94% (IR). The iodine color number of the acyl chloride is 20. Both the acyl chloride and the catalyst are phosgene-free.

EXAMPLE 13

In a thermostated 5 l reactor, 1,120 g (4 moles) of technical grade talloleic acid (mixture of mono-unsaturated and polyunsaturated $C_{18}$-carboxylic acids) and 147 g (0.8 mole) of activated diethylformamide are initially taken at 70° C. 390 g (3.94 moles) of gaseous phosgene are then passed in uniformly over 2.0 hours with thorough stirring. The internal temperature during the addition of phosgene is from 72° to 74° C. The waste gas from the reaction is removed directly via a scrubber After the end of the reaction, the vapor space above the reaction mixture is phosgene-free.

Stirring is then continued for 1.0 hour at 72° C., the stirrer is switched off and the reaction mixture is cooled to 20° C. At this temperature, the lower catalyst phase (141 g of activated DEF) is separated off from the two-phase reaction mixture after 1.5 hours. The upper phase contains 1,188 g of talloleic acid chloride (99.5% yield, based on talloleic acid used) having a purity of 92% (IR). The iodine color number of the acyl chloride is 100. Both the acyl chloride and the catalyst are phosgene-free.

COMPARATIVE EXAMPLE A

In a thermostated reactor, 1,946 g (7 moles) of technical grade stearic acid are melted at from 60° to 65° C. and 12.8 g (0.175 mole) of dimethylformamide (DMF) are added. Gaseous phosgene is then passed in uniformly over 3.0 hours with thorough stirring until an on-spec acyl chloride is obtained. The internal temperature during the addition of phosgene is kept at from 60° to 65° C. The required amount of phosgene is 940 g (9.5 moles).

The acyl chloride contains phosgene, and is dephosgenated with dry nitrogen in the course of 12 hours at room temperature. During this procedure, the catalyst separated out as a solid. After filtration, 2,025 g (97.6% yield) of stearyl chloride having a purity of 98% are obtained.

COMPARATIVE EXAMPLE B

Similar to DE-A-29 50 155

1,355 g (5.0 moles) of technical grade stearic acid are melted at 60° C. and 2.7 g (0.0172 mole) of diisobutylformaide are added. The apparatus has a reflux condenser (coolant temperature −20° C.) with a downstream scrubber. Gaseous phosgene is passed in at from 60° to 65° C. with thorough stirring until conversion of the stearic acid to the acyl chloride is complete. The phosgene is metered in such a way that there is only an extremely small phosgene reflux in the reflux condenser. 781 g (7.9 moles) of phosgene are required. The addition of phosgene takes 9 hours.

The phosgene-containing stearyl chloride is dephosgenated with dry nitrogen in the course of 3 hours at 60° C. The reaction mixture remains homogeneous. The amount of crude acyl chloride discharged is 1,435 g (maximum possible yield of stearyl chloride 1,448 g), the purity being 96% (IR). The iodine color number of the brown product is 100.

We claim:

1. In a process for the preparation of an acyl chloride of the formula

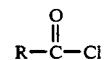

where R is $C_8$–$C_{30}$-alkyl, $C_3$–$C_{30}$-alkenyl or $C_8$–$C_{30}$-alkynyl, comprising reacting a carboxylic acid of the formula

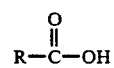

where R has the above-mentioned meanings, and phosgene, $COCl_2$ (III), in the presence of a catalyst adduct of phosgene and an N,N-dialkylformamide of the formula

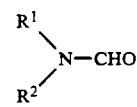

where $R^1$ and $R^2$ independently of one another are each $C_1$–$C_3$-alkyl, the improvement which comprises:
  carrying out the reaction with the carboxylic acid II and the phosgene III reactants in substantially equimolar amounts while using said catalyst adduct in an amount of from 5 to 200 mol %, based on the carboxylic acid II;
  allowing the reaction mixture containing the acyl chloride I product to separate into two phases;
  separating the lower phase formed by the catalyst adduct from the upper product phase; and
  reusing the lower phase containing the catalyst adduct.

2. A process as claimed in claim 1, wherein the N,N-dialkylformamide used is N,N-dimethylformamide, methylethylformamide or diethylformamide.

3. A process as claimed in claim 1, wherein the N,N-dialkylformamide used in N,N-diethylformamide.

4. A process as claimed in claim 1, wherein from 10 to 100 mol % of the catalyst adduct are used.

5. A process as claimed in claim 1, wherein from 10 to 30 mol % of the catalyst adduct are used.

6. A process as claimed in claim 1, wherein the catalyst adduct used is a 1:1 adduct in excess N,N-dialkylformamide.

7. A process as claimed in claim 4, wherein the catalyst adduct used is a 1:1 adduct in excess N,N-dialkylformamide.

8. A process as claimed in claim 1, wherein the reaction is carried out at 0° to 200° C. and the phase separation is carried out at 0° to 150° C.

9. A process as claimed in claim 1, wherein the reaction is carried out at 30° to 100° C. and the phase separation is carried out at 20° to 50° C.

10. A process as claimed in claim 5, wherein the catalyst adduct used is a 1:1 adduct in excess N,N-dialkylformamide.

* * * * *